United States Patent [19]
Jones et al.

[11] Patent Number: 5,910,270
[45] Date of Patent: Jun. 8, 1999

[54] VISCOSITY REDUCTION OF ORGANOMAGNESIUM SOLUTIONS

[75] Inventors: Paul D. Jones, South Salem, N.Y.;
Dennis B. Malpass, LaPorte, Tex.;
Gregory M. Smith, Bethel, Conn.

[73] Assignee: Akzo Nobel nv, Arnhem, Netherlands

[21] Appl. No.: 08/918,588

[22] Filed: Aug. 19, 1997

[51] Int. Cl.$^6$ ...................................................... C09R 3/00
[52] U.S. Cl. ............................... 252/182.3; 252/182.33; 252/182.34
[58] Field of Search ........................... 252/182.3, 182.34; 502/152, 153; 556/410, 412, 480, 418; 260/665

[56] References Cited

U.S. PATENT DOCUMENTS

| | | | |
|---|---|---|---|
| 3,264,360 | 8/1966 | Nudenberg et al. | 260/665 G |
| 3,737,393 | 6/1973 | de Vries | 260/665 G |
| 4,299,781 | 11/1981 | Fannin et al. | 260/665 R |
| 4,383,119 | 5/1983 | Pullukat et al. | 556/412 |
| 4,477,587 | 10/1984 | Band | 502/125 |
| 4,490,513 | 12/1984 | Minami et al. | 502/116 |
| 4,544,646 | 10/1985 | Pullukat et al. | 502/109 |
| 4,547,477 | 10/1985 | Malpass et al. | 502/153 |
| 4,707,462 | 11/1987 | Malpass et al. | 502/153 |
| 5,145,600 | 9/1992 | Kamienski et al. | 252/182.3 |
| 5,262,573 | 11/1993 | Smith et al. | 568/851 |
| 5,422,400 | 6/1995 | Kamiyama et al. | 525/240 |
| 5,470,812 | 11/1995 | Mink et al. | 502/125 |

*Primary Examiner*—Shean C. Wu
*Attorney, Agent, or Firm*—Richard P. Fennelly

[57] ABSTRACT

Hydrocarbon solutions of a dialkylmagnesium compound having reduced viscosity contain: (a) a hydrocarbon solvent; (b) a dialkylmagnesium compound normally soluble in hydrocarbon solvents; and (c) an effective viscosity reducing amount of a compound selected from the group consisting of a compound having silicon-oxygen bonding, a compound having silicon-nitrogen bonding, and mixtures thereof. Representative viscosity reducing agents include: tetraalkylorthosilicate compounds, such as those of the general formula $Si(OR)_4$, where R is an alkyl group containing from 1 to about 4 carbon atoms, as exemplified by tetraethylorthosilicate; alkylsilazane compounds, including a hexaalkyldisilazane compound containing from 1 to about 4 carbon atoms in the alkyl groups therein as exemplified by hexamethyldisilazane; and silicone oil.

12 Claims, No Drawings

VISCOSITY REDUCTION OF ORGANOMAGNESIUM SOLUTIONS

BACKGROUND OF THE INVENTION

Organomagnesium compounds, such as dialkylmagnesium compounds containing a total of from about five to about twenty carbon atoms in the two alkyl groups contained therein, have a tendency to oligomerize in hydrocarbon solution thereby resulting in an undesired viscosity increase in such solutions. U.S. Pat. No. 3,737,393 teaches that organoaluminum compounds can be utilized as a suitable class of viscosity reduction additives (for example, at a concentration of about 2 mole % aluminum based on the soluble magnesium content) for such organomagnesium solutions. This has been a commercially preferred technique for achieving the desired viscosity reduction, although it suffers from the disadvantage that aluminum is introduced as a hetero metal atom into the system which may often be an undesirable byproduct of the desired viscosity reduction effect.

A variety of other disclosures exist in the art in regard to how the viscosity of normally viscous solutions of organomagnesium compounds can be reduced as represented by the following references:

U.S. Pat. No. 4,299,781 advocates the use of organometallic compounds of gallium, indium, and lithium as representative viscosity reduction agents; and U.S. Pat. No. 4,547,477 indicates that a defined type of benzene derivative can be employed as a viscosity reduction agent.

SUMMARY OF THE INVENTION

The present invention relates to the reduction in the viscosity of a solution comprising an organomagnesium compound which comprises the use, as a viscosity reduction additive, of a compound containing a Si—O and/or Si—N bond.

DESCRIPTION OF THE PREFERRED EMBODIMENTS

The present invention pertains to low viscosity solutions of organomagnesium compounds in hydrocarbon solvents.

The term "hydrocarbon solvent" is used herein to designate aliphatic, cycloaliphatic and aromatic hydrocarbons. Illustrative of aliphatic solvents are n-pentane, isopentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and alpha-methylnaphthalene. Preferred solvents are those containing 5 to 20 carbon atoms, inclusive. More preferred are those containing 6 to 15 carbon atoms, inclusive. Particularly preferred solvents are those which have boiling points of from about 70° C. and about 110° C. The dialkylmagnesium compound is one which is normally soluble in such hydrocarbon solvents, but which also normally forms viscous solutions therein. Illustrative of such dialkylmagnesium compounds are butylmethylmagnesium, butylethylmagnesium, butyloctylmagnesium, di-n-amylmagnesium, diisoamylmagnesium, di-n-hexylmagnesium, di-n-octylmagnesium, and in general, dialkylmagnesium compounds in which the alkyl groups containing a total of 5 or more carbon atoms each, preferably 5 to 20 carbon atoms, and most preferably 5 to 12 carbon atoms. Also included in such dialkylmagnesium compounds are mixtures of two or more dialkylmagnesium compounds such as diisoamylmagnesium plus diethylmagnesium, or butylethylmagnesium plus di-n-hexylmagnesium.

The concentration of the dialkylmagnesium or mixture of dialkylmagnesium compounds in the solvent is not critical, and may vary over a wide range. In general, however, compositions according to this invention will contain one or more dialkylmagnesium compounds in an amount of from about 5 to about 90 mole percent of the overall composition, preferably from about 10 to about 60 mole percent.

The viscosity reducing agents which have been found effective according to this invention are those compounds which contain a silicon-oxygen or silicon-nitrogen bond. these respective compounds can be used either alone or in compatible admixtures. The chosen viscosity control compound can be present in the solution at from about 2 mole % to about 80 mole %, most preferably from about 5 mole % to about 25 mole %, relative to magnesium in solution. Generally speaking, the following types of viscosity reducing compounds are envisioned by the present invention:

Tetraalkylorthosilicates of the general formula $Si(OR)_4$ where R is an alkyl group which preferably contains from 1 to about 10 carbon atoms are a preferred type of additive for use herein. A representative, most preferred group of such compounds contain from 1 to about 4 carbon atoms in their alkyl groups. Tetraethylorthosilicate is the most preferred compound for selection in view of its ready availability and low cost.

Alkylsilazane compounds, as exemplified by hexaalkyldisilazane compounds containing from 1 to about 4 carbon atoms in their alkyl groups, form a suitable class of silicon-nitrogen additives which can be used in accordance with the present invention. A representative example for use is hexamethyldisilazane.

Silicone oils form yet another class of compound containing a silicon-oxygen bond which can be used in accordance with the present invention.

The silicon compounds may also contain aryl groups therein and mixtures of arylsilicon compounds with alkyl-silicon compounds are also considered to be useful in accordance with the present invention.

These additives for viscosity reduction all contain silicon which is a much more compatible heteroatom for introduction into the organomagnesium composition which will commonly be used in catalyst preparation procedures. Silicon-containing reagents are, in many instances, either used in such preparations or will function as a more benign composition if present during such procedures. These additives can be added directly to the organomagnesium compositions at room temperature, although, in certain instances, as in the case of the silicone oil compounds, elevated temperature treatment may be needed to achieve the desired results. The organosilicon compound may also be added during the process for producing the organomagnesium compound. Also, addition of organosilicon compounds may result in a reaction with the organomagnesium compound to make a derivative of the magnesium alkyl species. Nevertheless, the addition of the organosilicon compound, even if reactive with the organomagnesium compound, will achieve the desired result of reducing the viscosity of the resulting solution.

The invention is further illustrated by the following Examples.

EXAMPLES 1–10

Crude n-butylethylmagnesium (BEM) was obtained from Akzo Nobel Chemicals Inc. (Deer Park, Tex.) as a viscous (about 9000 cP) slurry of BEM and MgCl$_2$ in heptane. All experiments, with the exception of the viscosity measurements, were performed with a homogeneous mixture of BEM and MgCl$_2$. Tetraethylorthosilicate (TEOS) and hexamethyldisilazane (HMDS) were obtained from Aldrich and were used as received. Analyses and viscosities were performed on the clear supernatant liquid after allowing MgCl$_2$ to settle to the bottom of the container.

A series of BEM samples were prepared containing varying levels of viscosity reducer additive. These samples were prepared in 50 mL vials in a nitrogen-filled glove box. The samples were stirred with a polytetrafluoroethylene-coated magnetic stir bar until the viscosity reduction effect was complete (usually under five minutes). Table 1 summarizes the preparation of those samples which have TEOS as the selected viscosity reducer:

TABLE 1

Viscosity Reduction of BEM Solutions Using TEOS

| Example | Mole % TEOS (a) | wt % Mg | wt % Cl | Viscosity at 30° C. (cP) |
|---|---|---|---|---|
| 1 | 0.00 | 4.17 | 0.11 | 8760 |
| 2 | 11.0 | 3.97 | — | 450 |
| 3 | 15.0 | 4.44 | — | — |
| 4 | 20.0 | 4.05 | 0.03 | 20 |
| 5 | 27.1 | 3.76 | 0.02 | <20 |
| 6 | 35.4 | 5.35b | 0.03 | <20 |
| 7 | 35.4 | 3.61 | — | <20 |
| 8 | 40.3 | 3.64 | — | <20 |
| 9 | 62.3 | 2.91 | — | <20 |
| 10 | 83.8 | 1.11 | — | <20 | a = Mole % relative to soluble magnesium.
b = Erroneous Mg result. Example 7 was run as duplicate.

EXAMPLES 11–14

In these Examples, in a similar manner to Examples 1–10, the effect of hexamethyldisilazane (HMDS) as the viscosity reducing agent was measured. Table 2 summarizes the preparation of those samples:

TABLE 2

Viscosity Reduction of BEM Solutions Using HMDS

| Example | Mole % HMDS | wt % Mg | wt % Cl | Viscosity at 30° C. (cP) |
|---|---|---|---|---|
| 1* | 0 | 4.1 | 0.10 | 8760 |
| 11 | 10.0 | 3.90 | 0.09 | 35 |
| 12 | 15.0 | 4.11 | 0.09 | 20 |
| 13 | 20.0 | 3.81 | 0.10 | <20 |

*Inserted into Table 2 as a Comparative Example.

With these HMDS samples, gas evolution was seen upon stirring, presumably from the evolution of ethane and butane. As with the use of TEOS as the viscosity reduction additive, a typical reaction time was less than five minutes.

The foregoing Examples, since they are presented for illustrative purposes only to illustrate certain embodiments of the invention, should not be construed in a limiting sense. The scope of protection sought is set forth in the claims which follow.

We claim:

1. A hydrocarbon solution of a dialkylmagnesium compound having reduced viscosity, which solution comprises:
   (a) a hydrocarbon solvent;
   (b) a dialkylmagnesium compound normally soluble in hydrocarbon solvents; and
   (c) an effective viscosity reducing amount of a compound selected from the group consisting of a compound having silicon-oxygen bonding, a compound having silicon-nitrogen bonding, and mixtures thereof.

2. A hydrocarbon solution according to claim 1 in which the viscosity reducing agent is a tetraalkylorthosilicate.

3. A hydrocarbon solution according to claim 2 in which the tetraalkylorthosilicate of the general formula Si(OR)$_4$, where R is an alkyl group containing from 1 to about 4 carbon atoms.

4. A hydrocarbon solution according to claim 2 in which the tetraalkylorthosilicate is tetraethylorthosilicate.

5. A hydrocarbon solution according to claim 1 in which the viscosity reducing agent is an alkylsilazane compound.

6. A hydrocarbon solution according to claim 5 in which the viscosity reducing agent is a hexaalkyldisilazane compound containing from 1 to about 4 carbon atoms in the alkyl groups therein.

7. A hydrocarbon solution according to claim 5 in which the viscosity reducing agent is hexamethyldisilazane.

8. A hydrocarbon solution according to claim 1 in which the viscosity reducing agent is a silicone oil.

9. A hydrocarbon solution according to claim 1 in which the hydrocarbon solvent contains from 5 to 20 carbon atoms and wherein the viscosity reducing agent is a tetraalkylorthosilicate of the general formula Si(OR)$_4$, where R is an alkyl group containing from 1 to about 4 carbon atoms.

10. A hydrocarbon solution according to claim 9 in which the tetraalkylorthosilicate is tetraethylorthosilicate.

11. A hydrocarbon solution according to claim 1 in which the hydrocarbon solvent contains from 5 to 20 carbon atoms and wherein the viscosity reducing agent is a hexaalkyldisilazane compound containing from 1 to about 4 carbon atoms in the alkyl groups therein.

12. A hydrocarbon solution according to claim 11 in which the viscosity reducing agent is hexamethyldisilazane.

* * * * *